(12) United States Patent
Cheng et al.

(10) Patent No.: US 10,751,152 B2
(45) Date of Patent: Aug. 25, 2020

(54) JAW MOTION TRACKING SYSTEM AND OPERATING METHOD USING THE SAME

(71) Applicant: NATIONAL YANG-MING UNIVERSITY, Taipei (TW)

(72) Inventors: Liang-Yuan Cheng, Taipei (TW); Chih-Yu Hsu, Taipei (TW); Shyh-Yuan Lee, Taipei (TW); Yuan-Min Lin, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 245 days.

(21) Appl. No.: 15/387,072

(22) Filed: Dec. 21, 2016

(65) Prior Publication Data

US 2018/0168787 A1 Jun. 21, 2018

(51) Int. Cl.
*A61C 19/045* (2006.01)
*B33Y 80/00* (2015.01)
(Continued)

(52) U.S. Cl.
CPC .......... *A61C 19/045* (2013.01); *A61B 5/1114* (2013.01); *A61B 5/1127* (2013.01);
(Continued)

(58) Field of Classification Search
CPC .... A61C 19/045; H04N 13/254; B33Y 80/00; A61B 5/725; A61B 5/1128;
(Continued)

(56) References Cited

U.S. PATENT DOCUMENTS

| 4,836,778 A | * | 6/1989 | Baumrind | ............ | A61C 19/045 |
| | | | | | 356/139.03 |
| 5,143,086 A | * | 9/1992 | Duret | ................... | A61B 5/1127 |
| | | | | | 600/590 |

(Continued)

FOREIGN PATENT DOCUMENTS

| JP | 2006239104 A | * | 9/2006 | | |
| WO | WO-2007066842 A1 | * | 6/2007 | ........... | G05D 1/0251 |

OTHER PUBLICATIONS

Yuan F, Sui H, Li Z, Yang H, Lü P, Wang Y, et al. (2015) A Method of Three-Dimensional Recording of Mandibular Movement Based on Two-Dimensional Image Feature Extraction. PLoS ONE (Year: 2015).*

(Continued)

*Primary Examiner* — Richard A Hansell, Jr.
(74) *Attorney, Agent, or Firm* — Muncy, Geissler, Olds & Lowe, P.C.

(57) ABSTRACT

In this invention, a high-accuracy jaw motion tracking system and method using the same are disclosed. The jaw motion tracking system of the invention mainly comprises an eyewear facebow static positioning device, a lower jaw dynamic tracking device and a stereo-vision charge-coupled device (CCD) and can provide information regarding the locations and relative movement of lower and upper jaws. The eyewear facebow static positioning device has several passive and active reflective markers. The lower jaw dynamic tracking device equips with a plural of lightweight light emitting devices. Using OpenCV-based self-developed algorithm and post-iterative compensator, the disclosed system can record the dynamical jaw movement with a high accuracy. The disclosed jaw motion tracking system and related method have minimal occlusal disturbance and pro- (Continued)

vide smooth motion-tracking performance. The disclosed system can be used in clinical dentistry.

23 Claims, 5 Drawing Sheets (51) Int. Cl.
| | |
|---|---|
| *H04N 13/254* | (2018.01) |
| *H04N 13/239* | (2018.01) |
| *G01S 5/16* | (2006.01) |
| *A61B 5/00* | (2006.01) |
| *A61B 5/11* | (2006.01) |
| *G06T 7/285* | (2017.01) |

(52) U.S. Cl.
CPC .......... *A61B 5/4542* (2013.01); *A61B 5/6803* (2013.01); *B33Y 80/00* (2014.12); *G01S 5/16* (2013.01); *G06T 7/285* (2017.01); *H04N 13/239* (2018.05); *H04N 13/254* (2018.05); *A61B 5/725* (2013.01); *A61B 2560/0223* (2013.01); *A61B 2576/00* (2013.01); *G06T 2207/30036* (2013.01); *G06T 2207/30204* (2013.01)

(58) Field of Classification Search
CPC ........ A61B 2560/0223; A61B 2576/00; G06T 5/20; G06T 5/002; G06T 7/70; G06T 7/292
See application file for complete search history.

(56) References Cited

U.S. PATENT DOCUMENTS

| | | | | |
|---|---|---|---|---|
| 6,120,290 A * | 9/2000 | Fukushima | ............ | A61C 11/00 433/69 |
| 2007/0054235 A1* | 3/2007 | Rizoui | ................ | A61C 19/063 433/29 |
| 2009/0219386 A1* | 9/2009 | Ebisawa | ................ | A61B 5/163 348/78 |
| 2009/0305185 A1* | 12/2009 | Lauren | ................... | A61C 11/00 433/29 |
| 2010/0039500 A1* | 2/2010 | Bell | ..................... | H04N 13/239 348/46 |
| 2010/0179790 A1* | 7/2010 | Nakauchi | ............... | G02B 5/285 703/2 |
| 2013/0066598 A1* | 3/2013 | Fisker | .................... | A61C 11/00 703/1 |
| 2014/0058253 A1* | 2/2014 | Prough | ................ | A61B 5/0095 600/424 |
| 2015/0221084 A1* | 8/2015 | Adamson | ........... | A61B 1/00055 348/46 |
| 2016/0245916 A1* | 8/2016 | Weber-Grabau | ......... | G01V 8/20 |
| 2016/0262711 A1* | 9/2016 | Nyholm | ............... | A61B 5/0035 |
| 2017/0056236 A1* | 3/2017 | Yousefian | ................ | A61C 7/10 |
| 2017/0312065 A1* | 11/2017 | Marshall | ................ | A61B 5/682 |
| 2018/0055420 A1* | 3/2018 | Gassler | ................ | A61C 19/052 |
| 2018/0147039 A1* | 5/2018 | Carlson | .................... | A61B 5/00 |
| 2018/0262749 A1* | 9/2018 | Goldentouch | ........ | H04N 13/246 |
| 2019/0302091 A1* | 10/2019 | Kessler | ..................... | G06T 7/60 |

OTHER PUBLICATIONS

Planmeca Press Info "News | Planmeca 4DTM Jaw Motion tracking system announced" available at https://www.planmeca.com/na/press-info/news-room-main/planmeca-announces-advanced-planmeca-4d-jaw-motion-tracking-system/. According to WayBack Machine, the foregoing was made available as of Aug. 23, 2016 (Year: 2016).*

Cha et al. "An IR-based facial expression tracking sensor for head-mounted displays" Published in 2016 IEEE Sensors, Conference: Oct. 30-Nov. 3, 2016, Orlando, FL, USA, DOI: 10.1109/ICSENS.2016.7808913 (Year: 2016).*

Walid Hizem, Yang Ni, Bernadette Dorizzi. Near infrared sensing and associated landmark detection for face recognition. Journal of Electronic Imaging, Society of Photo-optical Instrumentation Engineers, 2008, 17 (1), pp. 011005-1-011005-7 . (Year: 2008).*

Furtado et al. "A specialized motion capture system for real-time analysis of mandibular movements using infrared cameras", BioMedical Engineering OnLine 2013, 12:17. (Year: 2013).*

Yanagisawa et al. "Tooth shape reconstruction from dental CT images with the region-growing method", Dentomaxillofacial Radiology (20140 43, 20140080 (Year: 2014).*

Hizem et al. "Near infrared sensing and associated landmark detection for face recognition" J. Electronic Imaging, Society of Photo-optical Instrumentation Engineers, 2008, 17 (1), pp. 011005-1-011005-7. (Year: 2008).*

Dang et al. "Continuous Stereo Self-Calibration by Camera Parameter Tracking", IEEE Transactions on Image Processing, vol. 18, No. 7, Jul. 2009 (Year: 2009).*

* cited by examiner

JAW MOTION TRACKING SYSTEM AND OPERATING METHOD USING THE SAME

BACKGROUND OF THE INVENTION

Field of the Invention

The present invention generally relates to a jaw motion tracking system, and more particularly a high-accuracy jaw motion tracking system and operating method using the same, with a light weight and a minimal occlusal disturbance.

Description of the Related Art

Jaw movements include opening and closing, protrusion, retrusion and lateral excursion of the mandible. Dentists use articulators to reduplicate the oral structures of the patient, and design and fabricate the dental prosthesis based on the model on the articulator. The components of the conventional articulator system include a facebow, which transfers the position of the temporo-mandibular joint and a bite record that registrants the maxilla-mandibular relationship. However, the jaw movement could not be perfectly recorded using an articulator.

The evolutions of facebow transfer are from arbitrary facebow, kinematic facebow to virtual facebow. (1) Arbitrary facebow is the traditional type that only can transfers the maxillary occlusal plane to an articulator statically. However, mandible movement contains six degree of freedom, thus arbitrary facebow and bite registration cannot represent the actual masticatory function of the patients. (2) The kinematic facebow, also called jaw-tracking device, was developed. Since 1896, a graphic recording method was first used to trace the mandibular movement. In general, there are numerous methods to trace the mandibular motion nowadays, such as graphical method, electromagnetic fields, video fluoroscopic, ultrasonic and optoelectronic devices. The goals to use jaw motion tracking devices and facebow transfer include (1) locating the related position of maxilla and mandible; (2) recording and simulating the mandibular movement; (3) assisting dentists to diagnosis and making the treatment plan and (4) facilitating the prosthesis design and fabrication for full mouth rehabilitation.

An electromagnetic method was used to monitor mandibular movements in three dimensions since 1975. The instrument equipped a permanent magnet lying in the inferior labial vestibule that secured to the mandible, and a magnetometer with the sensor arrays attached to a modified eyeglass worn by the patient, which sense changes in the magnetic field resulted from mandibular movement. The machine can only record three degrees of freedom. It cannot trace the rotations of the jaw.

An ultrasonic motion capture device was developed to record rigid body motion with six degrees of freedom at a sampling frequency of 75 Hz. The device contains three ultrasonic transmitters mounted on the lower jaw near the lower incisors and an upper frame with four receivers mounted on the head via face bow. Under the control of a computer, the ultrasonic pulses are radiated, and their runtimes from the transmitters to each of the receivers are measured by a software. Although the system is claimed with a accuracy less than 100 µm nowadays, it is too large and heavy that might interfere the movement of the patient as a result.

An optoelectronic device, able to lightweight and small, was first used to trace the motion of mandible since 1977. Normally, the optoelectronic system consists of three basic units: a passive or an active transmitter, e.g. light emitting diodes (LED) or reflective markers, one to three cameras as a receiver, and a computer with a camera interface and software to handle the extracted data. For example, product of JAWS-3D consists of a set of three orthogonal-oriented, one-dimensional, optoelectronic cameras, a control unit, and two triangular target frames (TTFs) with LEDs, rigidly connected to the upper and lower dental arches as the transmitters.

Several prototypes have been disclosed. For example, Fang and Kuo (2008) presented a system using a pair of CCD cameras and three LEDs fixed to a pair of tracking plates attached on upper and lower anterior teeth for 3D reconstruction. Furtado, D. A., et al. (2013) used three infrared cameras and a set of nine reflective markers for mandibular motion capture. However, the transmitters of the instruments mentioned above are also too bulky and complicated. Adly et al. (2013) used two simple cube-shaped markers that have square black and white images on each sides which consist of two-dimensional (2D) barcodes and two cameras. Recently, Tanaka, Yuto, et al. (2016) reported a system and the related method to trace the masticatory movement without markers. The system comprising a laptop computer, data analysis software, and a camera capable of recording depth and red, green, and blue tracked depth data for each participant's face in real time and produced a computed 3D mask. Although the system was light and handy, the accuracy of the system still needs to be improved.

U.S. Pat. No. 5,143,086, issued to Duret entitled "Device for measuring and analyzing movements of the human body or of parts thereof" disclosed a device for determining mandibular motion wherein three light emitting diodes at the vertices of a triangle are temporarily fixed to teeth of the subject, the light emitting diodes are sequentially energized, and two sensors responsive to the light emitting diodes are mounted on a headpiece applied to the head of the subject and are trained on the light emitting diodes.

U.S. Pat. No. 8,794,962, issued to Lauren entitled "Methods and composition for tracking jaw motion". In the method, a plurality of microsphere targets is applied to a surface of a tooth on the upper dentition of a person and a tooth surface of the lower dentition of the person. At least two sets of stereoscopic images are obtained, where the microsphere targets are visible in the field of view of each image. The center position of the beads is photogrammetrically determined in three dimensions for each set using the images taken from perspective positions. The change in bead positions in the sets of stereoscopic images is analyzed to mathematically characterize the jaw motion of the person.

Ultrasonic-based jaw motion tracking devices and other developing optoelectronic devices of the prior art are typically heavy and may cause occlusal interference. Because the above-mentioned jaw motion tracking systems were either too complicated or not accurate enough for clinical dental applications, there is need to provide an invention regarding to a high-accuracy and light-weight jaw motion tracking system and the related operating method using the same.

BRIEF SUMMARY OF THE INVENTION

It is an objective of the present invention to provide a high-accuracy and light-weight jaw motion tracking system having minimal occlusal disturbance and providing smooth motion-tracking performance.

To achieve the above objective, the present invention provides a jaw motion tracking system, mainly comprising an eyewear facebow static positioning device, a lower jaw dynamic tracking device, and a stereo-vision charge-coupled device. The eyewear facebow static positioning device is equipped with a first plurality of light emitting device. The lower jaw dynamic tracking device is equipped with a second plurality of light emitting device. The stereo-vision charge-coupled device is equipped with two cameras set at two sides and an embedded microprocessor. The two cameras captures lights transmitted from the light emitting devices of the eyewear facebow static positioning device and the lower jaw dynamic tracking device and the embedded microprocessor reconstructs a three-dimensional world Euclidean coordinate. The first plurality of light emitting devices and the second plurality of light emitting devices are selected from an active light emitting device and a passive light emitting device.

According to one feature of the present invention, the first plurality of light emitting devices of the eyewear facebow static positioning device provide an 850 nm near-infrared light (or NIR light), and at least one of the plurality of light emitting devices is set at the center of the eyewear facebow static positioning device to be an original point to the lower jaw dynamic tracking device.

According to another feature of the present invention, the second plurality of light emitting devices of the lower jaw dynamic tracking device provide an 850 nm near-infrared light (or NIR light) and are made in the surface mounted type.

According to another feature of the present invention, the second plurality of light emitting devices of the lower jaw dynamic tracking device has four light emitting devices and the fourth light emitting device is used as an additional reference point to obtain a normal vector of a plane of the lower jaw dynamic tracking device.

According to another feature of the present invention, the embedded microprocessor in the stereo-vision charge-coupled device calibrates both intrinsic and extrinsic parameters of the camera of the stereo-vision charge-coupled device first when starting the jaw motion tracking system for every time.

It is another objective of the present invention to provide a high-accuracy operating method of the jaw motion tracking system having minimal occlusal disturbance and providing smooth motion-tracking performance.

To achieve the above objective, the present invention provides an operating method of the jaw motion tracking system, used for providing an information regarding locations and relative movements of lower and upper jaws of a patient. The operating method mainly comprises the steps of: wearing the eyewear facebow static positioning device on upper maxilla of the patient; bonding the lower jaw dynamic tracking device to the labial side of the lower incisors of the patient; capturing lights transmitted from the light emitting devices of the eyewear facebow static positioning device and the lower jaw dynamic tracking device by the two cameras of the stereo-vision charge-coupled device and reconstructing a first three-dimensional world Euclidean coordinate by the embedded microprocessor of the stereo-vision charge-coupled device; wherein the embedded microprocessor in the stereo-vision charge-coupled device calibrates both intrinsic and extrinsic parameters of the camera of the stereo-vision charge-coupled device first before reconstructing the first three-dimensional world Euclidean coordinate.

According to one feature of the present invention, the operating method further comprises the steps of: scanning a second three-dimensional world Euclidean coordinate of the lower jaw dynamic tracking device and the initial status of jaw by using a dental computer tomography; matching the first three-dimensional world Euclidean coordinate and the second three-dimensional world Euclidean coordinate to define an initial moving position of the lower jaw dynamic tracking device by using an iterative closest points algorithm in the embedded microprocessor; and recording a motion curve of the lower jaw dynamic tracking device.

According to another feature of the present invention, the operating method further comprises the steps of: smoothing the motion curve of the lower jaw dynamic tracking device by using a Kalman filter in the embedded microprocessor.

These and many other advantages and features of the present invention will be readily apparent to those skilled in the art from the following drawings and detailed descriptions.

BRIEF DESCRIPTION OF THE DRAWINGS

All the objects, advantages, and novel features of the invention will become more apparent from the following detailed descriptions when taken in conjunction with the accompanying drawings.

DETAILED DESCRIPTION OF THE INVENTION

Although the invention has been explained in relation to several preferred embodiments, the accompanying drawings and the following detailed descriptions are the preferred embodiment of the present invention. It is to be understood that the following disclosed descriptions will be examples of present invention, and will not limit the present invention into the drawings and the special embodiment.

Figure 1:
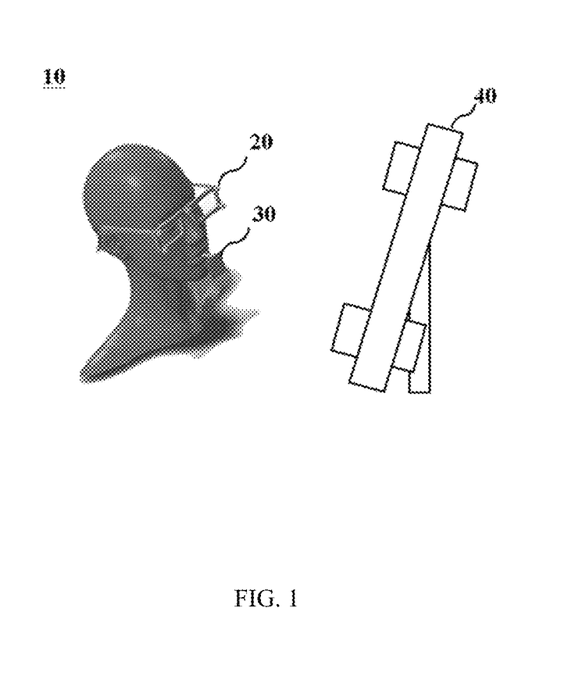
FIG. 1 shows the schematic diagram of the jaw motion tracking system of the present invention.

Please refer to FIG. 1, it shows the jaw motion tracking system of the present invention. The jaw motion tracking system 10 mainly comprises an eyewear facebow static positioning device 20, a lower jaw dynamic tracking device 30 and a stereo-vision charge-coupled device (CCD) 40. The jaw motion tracking system 10 can provide the information regarding the locations and relative movement of lower and upper jaws of a patient. The eyewear facebow static positioning device 20 and a lower jaw dynamic tracking device 30 are set as the transmitter of the jaw motion tracking system 10. The stereo-vision charge-coupled device 40 is set as the receiver of the jaw motion tracking system 10. The jaw motion tracking system 10 of this invention is optical based system. Since light disturbance in clinical environment is extremely strong, the problem must be solved. In the invention, the light source with 850 nm near-infrared light is used and can be detected by near-infrared (NIR) field cameras. The setup could prevent environmental light disturbance, such as surgical lamp and indoor lighting.

Figure 2A:
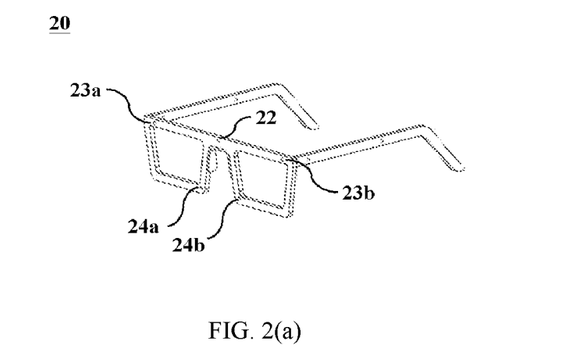
FIG. 2(a) shows the schematic diagram of the eyewear facebow static positioning device of the present invention.

Please refer to FIG. 2(a), it shows structure of the eyewear facebow static positioning device of the present invention. A reference structure that does not move during mandible movement is set when tracking the jaw movement. In this invention, the eyewear facebow static positioning device 20 is designed as the reference structure. The eyewear facebow static positioning device 20 is equipped with a plurality of light emitting devices such as light emitting device 22, light emitting device 23a, light emitting device 23b, light emitting device 24a and light emitting device 24b, and an external power supply. The eyewear facebow static positioning device 20 is used to represent the rigid body status of skull in Euclidean space. It is noted that in this invention, the light emitting device in the first plurality of light emitting devices has two types such as active light emitting device and passive light emitting device. The active light emitting device is typically the commercial light emitting diode (LED) which can emit to provide a light. The passive light emitting device is typically a light reflecting ball or a light reflecting lens which can not actively emit a light. The passive light emitting device reflects a light from an extra light source (not shown) to provide the light. In an embodiment, the light emitting device is selected from only the active light emitting device. In another embodiment, the light emitting device is selected from only the passive light emitting device. In another embodiment, the light emitting device is selected from combination of the active light emitting device and the passive light emitting device. Namely, the first plurality of light emitting devices are selected from an active light emitting device and a passive light emitting device. All of the plurality of light emitting devices, such as light emitting device 22, light emitting device 23a, light emitting device 23b, light emitting device 24a and light emitting device 24b, of the eyewear facebow static positioning device 20 provide an 850 nm near-infrared light. It is noted at least one of the plurality of light emitting devices, light emitting device 22, is set at the center of the eyewear facebow static positioning device 20 to be an original point to the lower jaw dynamic tracking device 30. The eyewear facebow static positioning device 20 is a glass type and is woar on the upper maxilla. Since the upper maxilla was part of the cranial bone, the eyewear facebow static positioning device 20 also represents the position of the maxilla.

Figure 2B:
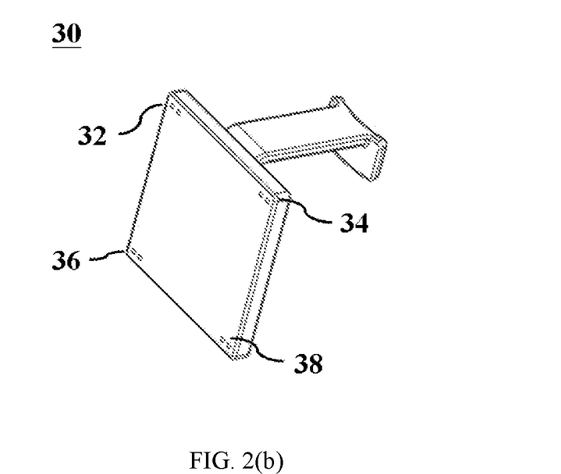
FIG. 2(b) shows the schematic diagram of the lower jaw dynamic tracking device of the present invention.

Please refer to FIG. 2(b), it shows structure of the lower jaw dynamic tracking device of the present invention. The lower jaw dynamic tracking device 30 is equipped with a plurality of light emitting devices such as light emitting device 32, light emitting device 34, light emitting device 36 and light emitting device 38, and an external power supply. It is also noted that in this invention, the light emitting device in the second plurality of light emitting devices has two types such as active light emitting device and passive light emitting device, as defined above. Similarly, the second plurality of light emitting devices are selected from an active light emitting device and a passive light emitting device. The number of the plurality of light emitting devices is at least three. In this embodiment, the numbers of the plurality of light emitting devices are four. All of the plurality of light emitting devices of the lower jaw dynamic tracking device 30 also provide an 850 nm near-infrared light and are made using the surface mounted type to be the surface mounted type. The lower jaw dynamic tracking device 30 can be formed by using many technologies, such as hot pressing, casting, module sintering and three-dimensional printing (3DP). Preferably, the lower jaw dynamic tracking device 30 is formed by using the three-dimensional printing. Thus, the lower jaw dynamic tracking device 30 has a weight as light as only 20 grams. The lower jaw dynamic tracking device 30 is bonded to the labial side of the lower incisors of a patient by using self-cured resin. Since the lower jaw dynamic tracking device 30 of the invention is small and lightweight, it is easy to equip and then the disturbance to jaw motion can be minimized, especially in class I and class III occlusion. Typically, the lower jaw dynamic tracking device 30 requires at least three light emitting devices markers to represent the rigid body of mandible in Euclidean space. Preferably, four light emitting devices are used to reconstruct the movement tracking of the lower jaw dynamic tracking device 30. The additional fourth light emitting device is the additional reference point to obtain the normal vector of a plane of the lower jaw dynamic tracking device 30 of the jaw motion tracking system 10.

Figure 2C:
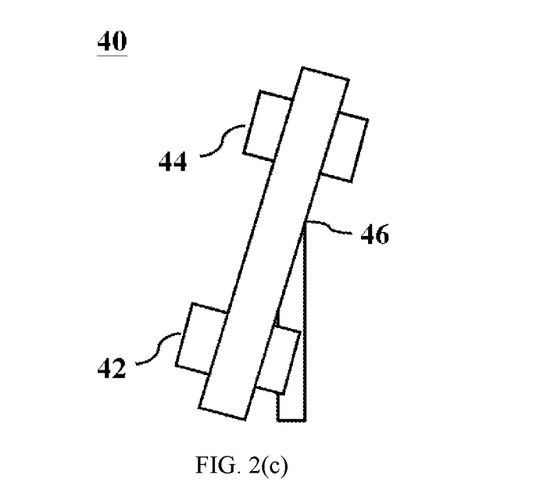
FIG. 2(c) shows the schematic diagram of the stereo-vision charge-coupled device (CCD) of the present invention.

Please refer to FIG. 2(c), it shows the stereo-vision charge-coupled device of the present invention. In this invention, the stereo-vision charge-coupled device 40 is used to capture the images flow and post-process to calculate the tracing curve of the lower jaw dynamic tracking device 30, displaying the mandibular movement of the patient. Two cameras, camera 42 and camera 44, are set in the left and right side of support 46 of the stereo-vision charge-coupled device 40, respectively. In the stereo vision reconstruction, the two cameras can capture the light form the light emitting devices of the eyewear facebow static positioning device 20 and the lower jaw dynamic tracking device 30. The stereo-vision charge-coupled device 40 has a highpass filter with a cutoff wavelength at 850 nm to achieve the NIR field spectrum upon 850 nm. An embedded microprocessor is designed in the stereo-vision charge-coupled device 40 to process the captured data, namely, an information regarding the lights transmitted from the light emitting devices of the eyewear facebow static positioning device 20 and the lower jaw dynamic tracking device 30, to reconstruct the three-dimensional world Euclidean coordinate of the eyewear facebow static positioning device 20 and the lower jaw dynamic tracking device 30.

The initial status for using the jaw motion tracking system 10 is making the upper jaw and the lower jaw in a center occlusion status. As shown in FIG. 1, by fixing the relative position of skull and the eyewear facebow static positioning device 20, the center light emitting device 22 of the eyewear facebow static positioning device 20 is set as the original point relative to the lower jaw dynamic tracking device 30. Thus, the disturbance caused by natural movement of patient can be eliminated. By applying the NIR field spectrum upon 850 nm, the feature of light emitting devices such as position of the eyewear facebow static positioning device 20 and the lower jaw dynamic tracking device 30 can be easily captured by the stereo-vision charge-coupled device 40. The disturbance from surgical lamp or other light sources are eliminated.

Figure 3:
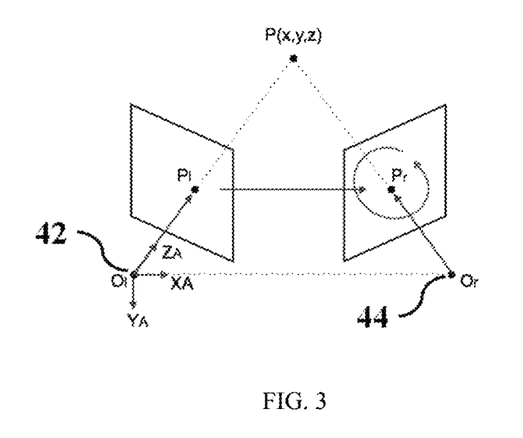
FIG. 3 shows coordinate diagram of the jaw motion tracking system of the present invention.

Please refer to FIG. 3, left camera's (camera 42) original point is set as default-original point of real world coordinate ($X_A$, $Y_A$, $Z_A$). Then the space translation and rotation matrix [R|t] of right camera (camera 44) relative to the left camera (camera 42) as FIG. 3 is obtained.

It is a feature of the present invention to use a triangulation method to measure three-dimensional points in space. By using the triangulation method in the microprocessor or a computer is embedded in the stereo-vision charge-coupled device 40, the three-dimensional points in space of the eyewear facebow static positioning device 20 and the lower jaw dynamic tracking device 30 can be measured by the triangulation method. In an embodiment, the stereo-vision charge-coupled device 40 can use the triangulation method with the linear transformation to rebuild the three-dimensional world Euclidean coordinate $[X\ Y\ Z\ 1]^T$ of arbitrary light emitting device in the eyewear facebow static positioning device 20 and the lower jaw dynamic tracking device 30 by giving the image plane coordinate $[u_1 v_1, 1]^T$ and $[u_2 v_2, 1]^T$ on $P_l$ and $P_r$, respectively.

Figure 4:
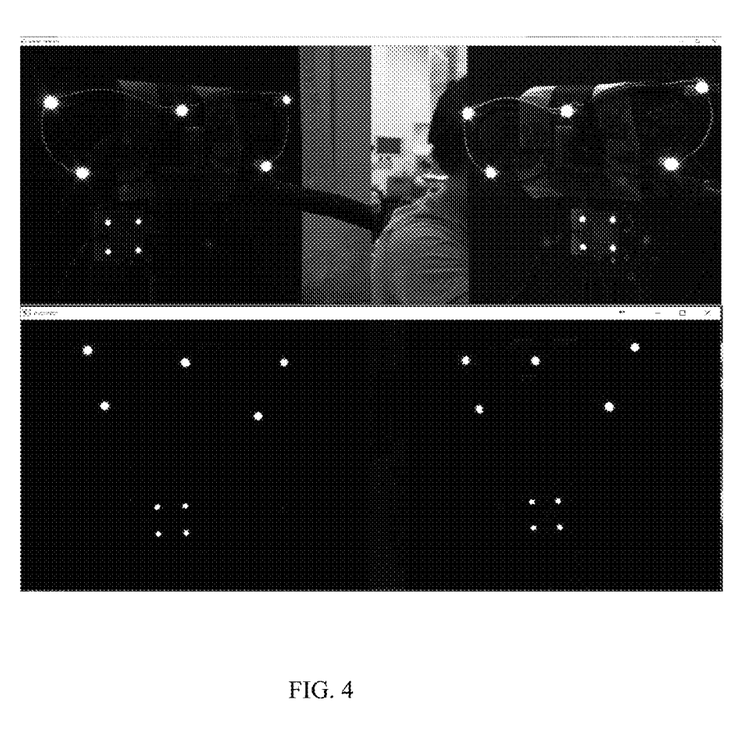
FIG. 4 shows stereo-imaging performed by the jaw motion tracking system when using (A) only normal NIR-field sampling and (B) a high-pass filter with a cutoff wavelength at 850 nm.

It is verified that the stereo-vision charge-coupled device 40 having the highpass filter with a cutoff wavelength at 850 nm can reduce the light disturbance in clinical environment. FIG. 4 shows stereo-imaging performed by the jaw motion tracking system 10 when using (A) only normal NIR-field sampling and (B) a high-pass filter with a cutoff wavelength at 850 nm.

It is also worthy to notice that both intrinsic and extrinsic parameters of the camera 42 and camera 44 need to be obtained precisely for accurately jaw motion tracking. Because every lens in the camera possesses certain levels of distortion, e.g. barrel distortion. Therefore, in this invention, a software of camera calibration is set in the embedded microprocessor of the stereo-vision charge-coupled device 40. When starting the jaw motion tracking system 10 for every time, both intrinsic and extrinsic parameters of the camera 42 and camera 44 of the stereo-vision charge-coupled device 40 are calibrated first. Namely, the intrinsic and extrinsic parameters of the camera 42 and camera 44 of the stereo-vision charge-coupled device 40 are calibrated first by capturing the lights form the eyewear facebow static positioning device 20 and the lower jaw dynamic tracking device 30 under the initial status for using the jaw motion tracking system 10. The software of camera calibration is based on OpenCV combined with self-interpreted calibration method. By using the self-interpreted calibration method of the present invention, the resolution of three-dimensional points in space of the eyewear facebow static positioning device 20 and the lower jaw dynamic tracking device 30 can achieve the sub-pixel level. The distortion error to sub-pixel level of the camera 42 and camera 44 of the stereo-vision charge-coupled device 40 can be closely minimized. The calibration result in re-projection error for the resolution of three-dimensional points in space is 0.19 pixel for each camera in planar coordinate of left and right image planes. In an embodiment, the camera 42 and the camera 44 are IDS UI-3240CP NIR (1.3 megapixel) with pixel size of 5.3 μm and resolution of 1280*1024. The working distance between the objects and the two cameras is larger than 30 cm and less than 50 cm. The objects are the light emitting device of the eyewear facebow static positioning device 20 such as light emitting device 22, light emitting device 23a, light emitting device 23b, light emitting device 24a and light emitting device 24b, and the lower jaw dynamic tracking device 30 such as light emitting device 32, light emitting device 34, light emitting device 36 and light emitting device 38. The squared chessboard in pose estimation is taken to obtain the distortion coefficient, and then to reconstruct the accurate 3D-space scale as possible. The distortion of any axis (X, Y and Z axis) of the objects should be minimized.

Figure 5:
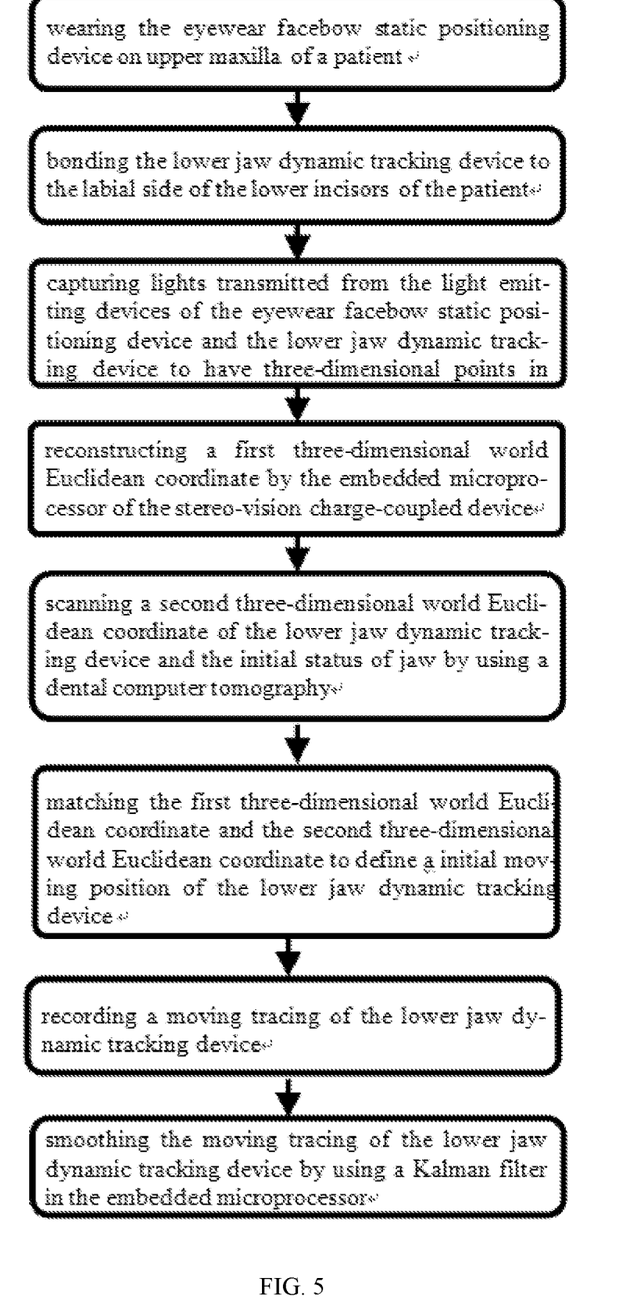
FIG. 5 shows flowchart of the operating method of the jaw motion tracking system of the present invention.

Please refer to FIG. 5, it shows flowchart of the operating method of the jaw motion tracking system of the present invention. The operating method of the jaw motion tracking system is used for providing an information regarding locations and relative movements of lower and upper jaws of a patient. The operating method mainly comprises the steps of:

Step 1: wearing the eyewear facebow static positioning device 20 on upper maxilla of the patient;

Step 2: bonding the lower jaw dynamic tracking device 30 to the labial side of the lower incisors of the patient;

Step 3: capturing lights transmitted from the light emitting devices of the eyewear facebow static positioning device 20 and the lower jaw dynamic tracking device 30 by the two cameras of the stereo-vision charge-coupled device 40 to have three-dimensional points;

Step 4: reconstructing a first three-dimensional world Euclidean coordinate by the embedded microprocessor of the stereo-vision charge-coupled device 40 from the three-dimensional points.

The operating method further comprises the steps of:

Step 5: scanning a second three-dimensional world Euclidean coordinate of the lower jaw dynamic tracking device 30 and the initial status of jaw by using a dental computer tomography;

Step 6: matching the first three-dimensional world Euclidean coordinate and the second three-dimensional world Euclidean coordinate to define an initial moving position of the lower jaw dynamic tracking device 30 by using an iterative closest points algorithm in the embedded microprocessor;

Step 7: recording a motion curve of the lower jaw dynamic tracking device 30; and Step 8: smoothing the motion curve of the lower jaw dynamic tracking device 30 by using a Kalman filter in the embedded microprocessor.

In FIG. 5, the order of step 1 and step 2 can be changed. In the step 4 of reconstructing a first three-dimensional world Euclidean coordinate by the embedded microprocessor of the stereo-vision charge-coupled device 40 further comprises of the steps of:

using a triangulation method with the linear transformation to rebuild the first three-dimensional world Euclidean coordinate from the three-dimensional points in space.

It is noted that when processing step 3, the embedded microprocessor in the stereo-vision charge-coupled device 40 calibrates both intrinsic and extrinsic parameters of the camera of the stereo-vision charge-coupled device first, after step 3 of capturing lights transmitted from the light emitting devices of the eyewear facebow static positioning device 20 and the lower jaw dynamic tracking device 30 by the two cameras of the stereo-vision charge-coupled device 40 and before step 4 of reconstructing a first three-dimensional world Euclidean coordinate by the embedded microprocessor of the stereo-vision charge-coupled device, when starting the jaw motion tracking system for every time. The software of camera calibration is based on OpenCV combined with self-interpreted calibration method.

Once the step 4 of the re-construction is done, step 5 to step 7 are the process of tracing and recording. The Kalman filter in step 8 is used to de-noising the mismatched calculation points and smoothing the tracing curve before recording. It is also noted the step 8 can be also used after the step 3.

One of the improvements of the jaw motion tracking system 10 is the simple feature registration module as disclosed in FIG. 1 and the simple and accuracy feature registration method as disclosed in step 1 to step 8. It is noted that the feature registration module is software type based on the OpenCV-based algorithm. The relevant OpenCV application interface (API) is cv2.correctmatch. In order to obtain the best result of this application interface, several front works to rectify the dual-images and access the result of undistorted images can be used or not. The front works are relatively complicated.

The one important feature of the present invention is disclosed as following. After setting the jaw motion tracking system 10, the measured results of the three-dimensional world Euclidean coordinate done during the step 5 to step 7 are used again as post-compensation to optimizing the calibration result in the step 3 and step 4. The motorizing stage can feed back the definitely correct result of sapling point. The measured results of the three-dimensional world Euclidean coordinate are used to obtain several parameters after calibration. One of them is the scale ratio error, that caused on the front-end physical scale of calibration board or omitted values during numerical calculations.

In the embodiment, the accuracy of the jaw motion tracking system 10 was shown. In the setup, the eyewear facebow static positioning device 20 should be at the original coordinate relative to the lower jaw dynamic tracking device 30. Motorized linear stage and rotary stage is made by Zaber Technologies Inc., Canada, in a embodiment, and was used to examine the accuracy of the jaw motion tracking system 10 by comparing the paths of the motorized stages and paths obtained from the eyewear facebow static positioning device 20 and the lower jaw dynamic tracking device 30. The resolution of the motorized stages is 0.1 micron and 0.01 degree. The system can obtain the relative movement and status between the eyewear facebow static positioning device 20 and the lower jaw dynamic tracking device 30, which also represent the relative movement of upper jaw and lower jaw by defining the plane position coordinates and normal vector.

The experiments of the jaw motion tracking system 10 can be divided into several parts. The first part aimed to examine the displacement errors of the eyewear facebow static positioning device 20. The mass center of the lower jaw dynamic tracking device 30 was recorded by comparing with the output of motorized linear stages. Table 1 shows the experimental Procedure for testing the jaw motion tracking system In experiment 1, the motorized stage moved in the following order: 25 mm in X axis, 25 mm in Y axis and 25 mm in Z axis from the original point. Different step distance and latency are set to examine the accuracy of this system. This part can be explained as tracing the movement of linear stages in full speed (8.8 mm/sec, 0.5 mm step), slower speed (3.4 mm/sec, 0.2 mm/step) and delicate scanning scale speed (0.1 mm/sec, 0.05 mm step).

The stage then moved back to the start point in same sequence to form a loop-like trace. The test was repeated for 5 times in 3 different speeds, and the repeatability and correlation coefficients between two datasets (stereo vision system and output of linear stages) shown below.

Experiment 2 examined the rotation movement. The rotation movement is calculated by every single feature point, and it is needed to convert the linear errors into angular errors.

Experiment 3 combines the movement of rotation and translation. In real mandible movement, lower jaw is a non-linear model combined with rotation and translation. Therefore, this experiment is set as demonstration of the present system of the invention that simulated by rotation and translation stages.

TABLE 1

The experimental Procedure for testing the jaw motion tracking system

| | Movement sequence | displacement | speed | step |
|---|---|---|---|---|
| Experiment 1 | Translation with different speed (Tx + Ty + Tz) | Tx 25 mm→Ty 25 mm→Tz 25 mm | 1. 0.1 mm/sec 2. 3.4 mm/sec 3. 8.8 mm/sec | 1. 0.05 mm/step 2. 0.4 mm/step 3. 0.5 mm/step |
| Experiment 2 | Rotation (Rx) | Rx 0° to +35° | 1.5°/sec | 0.5°/step |
| Experiment 3 | Rotation and Translation (Rx + Tz) | Rx −15° to +25° →Tz 10 mm | 1.5°/sec | 0.5°/step |

Due to the simple characteristics of small sized light emitting devices in the eyewear facebow static positioning device 20 and the lower jaw dynamic tracking device 30, the jaw motion tracking system 10 can easily set the image coordinate as index to re-sequence and match the definitely correct matches on reconstructing.

In order to explore the correlation of two datasets obtained in step 5 and step 6, the time clock to each dataset is set to align the correspondence points. The absolute distances of two datasets relative to the original points of this Euclidean space are simply calculated to obtain the correlation coefficients. The result was shown in Table. 2

TABLE 2

Correlation coefficients of stage output and measurement data

| | Measurements | |
|---|---|---|
| Stage Output | Norm [stage] | Norm [measurement] |
| Norm [stage] | 1.000000 | 0.993262 |
| Norm [measurement] | 0.993245 | 1.000000 |

Figure 6:
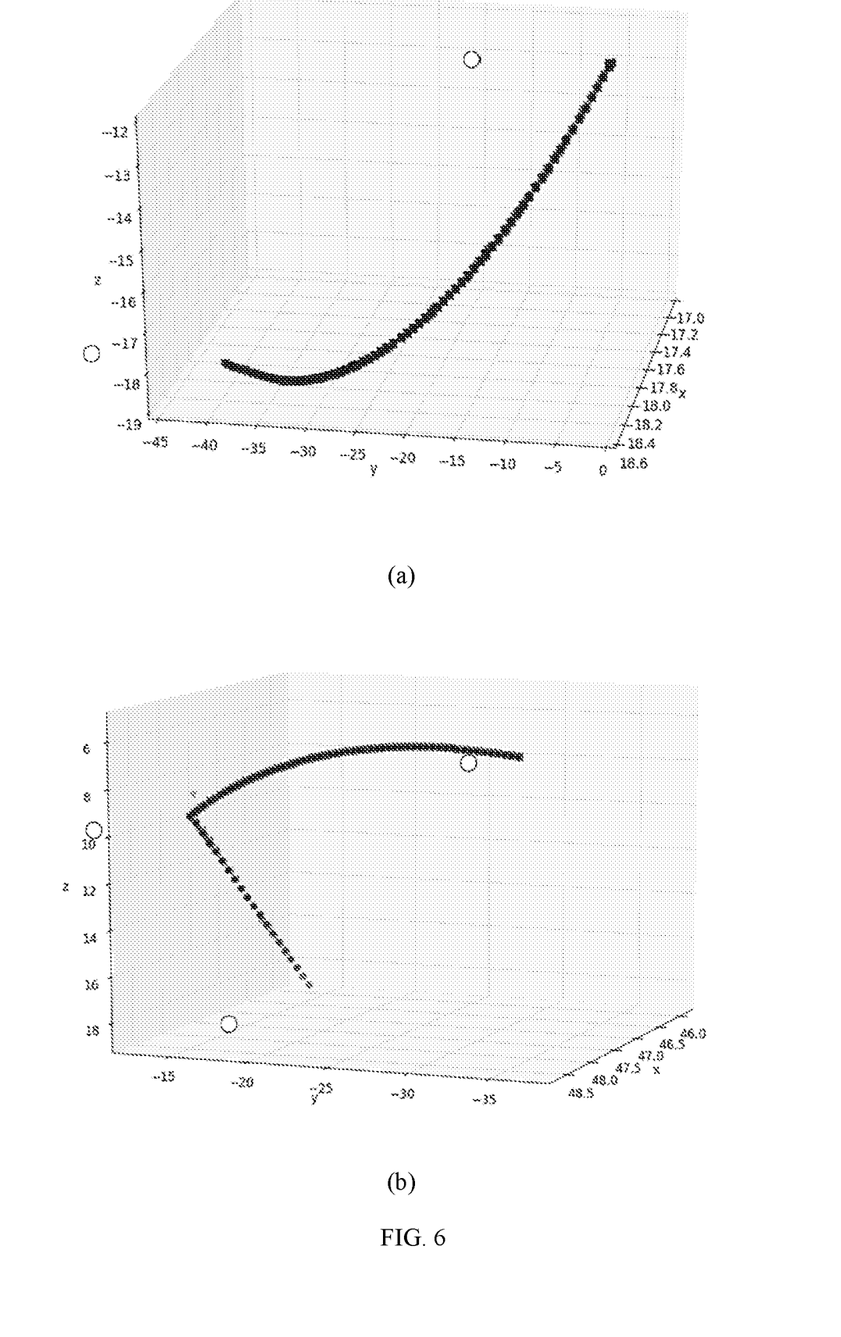
FIG. 6 shows the correlation and repeatability of 5 experimental repeats, and the mean error between 5 experiments can be down-axis into one parameter in 0.05847 mm. (a) The plot of tracking data in rotation of 35°, 0.5°/step and 5 experimental repeats of Stereo vision Data, and (b) the plot of 5 experimental repeats of stereo vision data rotating in 40°, 0.5°/step, then translate 10 mm in 0.5 mm/step.

FIG. 6 showed the correlation and repeatability of 5 experimental repeats, and the mean error between 5 experiments can be down-axis into one parameter in 0.05847 mm. (a) The plot of tracking data in rotation of 35°, 0.5°/step and 5 experimental repeats of Stereo vision Data, and (b) the plot of 5 experimental repeats of stereo vision data rotating in 40°, 0.5°/step, then translate 10 mm in 0.5 mm/step.

Table 3, 4 and 5 show the errors and repeatability in each axis in detail. RMS error related in stage and vision data are synchronized by computer clock. Mean error of 5 experiments is the average down-sampled data. For the repeatability, the position 6 endpoints (marked with white dots) in the loop are taken, and the standard deviation of 5 different experiments are calculated. At the last, the mean standard deviation of each endpoint, these results are taken as post compensator to calibrate the scale ratio.

TABLE 3

Error Table of Displacement Measurements
at 0.1 mm/sec, 0.05 mm step (unit: mm)

|  | RMS error related in stage and vision data | Mean error of 5 Experiments | Repeatability of 5 Experiments | Mean Standard Deviation of each Endpoints |
|---|---|---|---|---|
| X axis | 0.0502 | 0.0488 | 0.0016 | 0.02524 |
| Y axis | 0.0311 | 0.0349 | 0.0079 | 0.0442 |
| Z axis | 0.0882 | 0.0917 | 0.0121 | 0.0966 |

TABLE 4

Error Table of Displacement Measurements
at 3.4 mm/sec, 0.4 mm step (unit: mm)

|  | RMS error related in stage and vision data | Mean error of 5 Experiments | Repeatability of 5 Experiments | Mean Standard Deviation of each Endpoints |
|---|---|---|---|---|
| X axis | 0.0510 | 0.0892 | 0.0022 | 0.0260 |
| Y axis | 0.0431 | 0.0612 | 0.0102 | 0.0427 |
| Z axis | 0.1012 | 0.0677 | 0.0094 | 0.0796 |

TABLE 5

Error Table of Displacement Measurements
at 8.8 mm/sec, 0.5 mm step (unit: mm)

|  | RMS error related in stage and vision data | Mean error of 5 Experiments | Repeatability of 5 Experiments | Mean Standard Deviation of each Endpoints |
|---|---|---|---|---|
| X axis | 0.0709 | 0.133 | 0.00417 | 0.0372 |
| Y axis | 0.0566 | 0.0788 | 0.0116 | 0.0455 |
| Z axis | 0.0983 | 0.1166 | 0.0130 | 0.1021 |

According to the present invention, it is found that the advantages of the present invention are to provide a high-accuracy and light-weight jaw motion tracking system having minimal occlusal disturbance and providing smooth motion-tracking performance. Therefore, the disclosed system can be used in clinical dentistry.

Although the invention has been explained in relation to its preferred embodiment, it is not used to limit the invention. It is to be understood that many other possible modifications and variations can be made by those skilled in the art without departing from the spirit and scope of the invention as hereinafter claimed.

What is claimed is:

1. A jaw motion tracking system, mainly comprising:
an eyewear facebow static positioning device, equipped with a first plurality of light emitting devices;
a lower jaw dynamic tracking device, equipped with a second plurality of light emitting devices; and
a stereo-vision charge-coupled device, equipped with two cameras set at two sides and an embedded microprocessor, the two cameras capturing lights transmitted from the light emitting devices of the eyewear facebow static positioning device and the lower jaw dynamic tracking device and the embedded microprocessor reconstructing a three-dimensional world Euclidean coordinate;
wherein the first plurality of light emitting devices and the second plurality of light emitting devices are selected from an active light emitting device and a passive light emitting device; and
the embedded microprocessor uses a software of camera calibration to calibrate both intrinsic and extrinsic parameters of the camera of the stereo-vision charge-coupled device before reconstructing the three-dimensional world Euclidean coordinate.

2. A jaw motion tracking system as claimed in claim 1, wherein the first plurality of light emitting devices of the eyewear facebow static positioning device provide an 850 nm near-infrared light (or NIR light).

3. A jaw motion tracking system as claimed in claim 1, wherein at least one of the plurality of light emitting devices is set at the center of the eyewear facebow static positioning device.

4. A jaw motion tracking system as claimed in claim 1, wherein the second plurality of light emitting devices of the lower jaw dynamic tracking device provide an 850 nm near-infrared light (or NIR light) and are made in the surface mounted type.

5. A jaw motion tracking system as claimed in claim 1, wherein the second plurality of light emitting devices of the lower jaw dynamic tracking device has four light emitting devices and the fourth light emitting device is used as an additional reference point to obtain a normal vector of a plane of the lower jaw dynamic tracking device.

6. A jaw motion tracking system as claimed in claim 1, wherein the lower jaw dynamic tracking device is formed by using three-dimensional printing.

7. A jaw motion tracking system as claimed in claim 1, wherein the stereo-vision charge-coupled device has a high-pass filter with a cutoff wavelength at 850 nm to achieve a NIR field spectrum upon 850 nm.

8. A jaw motion tracking system as claimed in claim 1, wherein the embedded microprocessor calibrates both intrinsic and extrinsic parameters of the camera of the stereo-vision charge-coupled device first when starting the jaw motion tracking system for every time.

9. A jaw motion tracking system as claimed in claim 1, wherein the embedded microprocessor in the stereo-vision charge-coupled device uses a triangulation method with the linear transformation to reconstruct the three-dimensional world Euclidean coordinate.

10. A jaw motion tracking system as claimed in claim 1, wherein the embedded microprocessor uses the software of camera calibration based on OpenCV combined with self-interpreted calibration method to calibrate both intrinsic and extrinsic parameters of the camera of the stereo-vision charge-coupled device.

11. A jaw motion tracking system as claimed in claim 1, wherein the active light emitting device is a light emitting diode (LED) which emits to provide a light, and the passive light emitting device is a light reflecting ball or a light reflecting lens which reflects a light from an extra light source to provide the light.

12. An operating method of the jaw motion tracking system, used for providing an information regarding locations and relative movements of lower and upper jaws of a patient, the jaw motion tracking system mainly comprising an eyewear facebow static positioning device equipped with a first plurality of light emitting devices, a lower jaw dynamic tracking device equipped with a second plurality of light emitting devices and a stereo-vision charge-coupled device equipped with two cameras set at two sides and an embedded microprocessor, the first plurality of light emitting devices and the second plurality of light emitting devices are selected from an active light emitting device and a passive light emitting device, the operating method mainly comprising the steps of:

wearing the eyewear facebow static positioning device on upper maxilla of the patient;

bonding the lower jaw dynamic tracking device to the labial side of the lower incisors of the patient;

capturing lights transmitted from the light emitting devices of the eyewear facebow static positioning device and the lower jaw dynamic tracking device by the two cameras of the stereo-vision charge-coupled device, and reconstructing a first three-dimensional world Euclidean coordinate by the embedded microprocessor of the stereo-vision charge-coupled device;

wherein the embedded microprocessor uses a software of camera calibration to calibrate both intrinsic and extrinsic parameters of the camera of the stereo-vision charge-coupled device before reconstructing the first three-dimensional world Euclidean coordinate.

13. An operating method of jaw motion tracking system as claimed in claim 12, wherein the step of wearing the eyewear facebow static positioning device and the step of bonding the lower jaw dynamic tracking device are exchanged.

14. An operating method of jaw motion tracking system as claimed in claim 12, wherein capturing lights transmitted from the light emitting devices of the eyewear facebow static positioning device and the lower jaw dynamic tracking device further comprises:

making the upper jaw and the lower jaw in a center occlusion status.

15. An operating method of jaw motion tracking system as claimed in claim 12, wherein the step of reconstructing a first three-dimensional world Euclidean coordinate by the embedded microprocessor of the stereo-vision charge-coupled device further comprising of the steps of:

using a triangulation method with the linear transformation to rebuild the first three-dimensional world Euclidean coordinate.

16. An operating method of jaw motion tracking system as claimed in claim 12 wherein the embedded microprocessor uses the software of camera calibration based on OpenCV combined with self-interpreted calibration method to calibrate both intrinsic and extrinsic parameters of the camera of the stereo-vision charge-coupled device.

17. An operating method of jaw motion tracking system as claimed in claim 12, further comprising the steps of:

scanning a second three-dimensional world Euclidean coordinate of the lower jaw dynamic tracking device by using a dental computer tomography;

matching the first three-dimensional world Euclidean coordinate and the second three-dimensional world Euclidean coordinate to define an initial moving position of the lower jaw dynamic tracking device by using an iterative closest points algorithm in the embedded microprocessor; and recording a motion curve of the lower jaw dynamic tracking device.

18. An operating method of jaw motion tracking system as claimed in claim 17, further comprising the steps of:

smoothing the motion curve of the lower jaw dynamic tracking device by using a Kalman filter in the embedded microprocessor.

19. An operating method of jaw motion tracking system as claimed in claim 12, wherein the first plurality of light emitting devices of the eyewear facebow static positioning device provide an 850 nm near-infrared light (or NIR light) and at least one of the plurality of light emitting devices is set at the center of the eyewear facebow static positioning device.

20. An operating method of jaw motion tracking system as claimed in claim 12, wherein the second plurality of light emitting devices of the lower jaw dynamic tracking device provide an 850 nm near-infrared light (or NIR light) and are made in the surface mounted type.

21. An operating method of jaw motion tracking system as claimed in claim 12, wherein the second plurality of light emitting devices of the lower jaw dynamic tracking device has four light emitting devices and the fourth light emitting device is used as an additional reference point to obtain a normal vector of a plane of the lower jaw dynamic tracking device.

22. An operating method of jaw motion tracking system as claimed in claim 12, wherein the stereo-vision charge-coupled device has a highpass filter with a cutoff wavelength at 850 nm to achieve a NIR field spectrum upon 850 nm.

23. An operating method of jaw motion tracking system as claimed in claim 12, wherein the active light emitting device is a light emitting diode (LED) which emits to provide a light, and the passive light emitting device is a light reflecting ball or a light reflecting lens which reflects a light from an extra light source to provide a light.

* * * * *